United States Patent
Lee et al.

(10) Patent No.: US 10,253,341 B2
(45) Date of Patent: Apr. 9, 2019

(54) **MUTANT SUGAR ISOMERASE WITH IMPROVED ACTIVITY, DERIVED FROM *E. COLI*, AND PRODUCTION OF L-GULOSE USING THE SAME**

(71) Applicant: KONKUK UNIVERSITY INDUSTRIAL COOPERATION CORP., Seoul (KR)

(72) Inventors: Jung-Kul Lee, Seoul (KR); Chandra Sujan Sigdel, Seoul (KR); Jinglin Li, Seoul (KR); Tae-Su Kim, Seoul (KR)

(73) Assignee: KONKUK UNIVERSITY INDUSTRIAL COOPERATION CORP., Seoul (KR)

( * ) Notice: Subject to any disclaimer, the term of this patent is extended or adjusted under 35 U.S.C. 154(b) by 0 days.

(21) Appl. No.: 15/318,172

(22) PCT Filed: Jun. 13, 2014

(86) PCT No.: PCT/KR2014/005218
§ 371 (c)(1),
(2) Date: Dec. 12, 2016

(87) PCT Pub. No.: WO2015/190633
PCT Pub. Date: Dec. 17, 2015

(65) Prior Publication Data
US 2017/0191098 A1    Jul. 6, 2017

(30) Foreign Application Priority Data
Jun. 12, 2014  (KR) .......................... 10-2014-0071473

(51) Int. Cl.
*C12N 9/90* (2006.01)
*C12P 19/02* (2006.01)
*C12P 19/24* (2006.01)

(52) U.S. Cl.
CPC .............. *C12P 19/02* (2013.01); *C12P 19/24* (2013.01); *C12N 9/90* (2013.01)

(58) Field of Classification Search
None
See application file for complete search history.

(56) References Cited

U.S. PATENT DOCUMENTS

| 2009/0181854 A1 | 7/2009 | Thorson et al. | |
| 2013/0004998 A1* | 1/2013 | Subbian .................. | C12N 9/90 435/106 |

FOREIGN PATENT DOCUMENTS

| KR | 10-0512062 B1 | 1/2006 |
| KR | 10-2009-0081435 A | 5/2014 |
| WO | WO 2008/020659 A1 * | 2/2008 |

OTHER PUBLICATIONS

Laura M. van Staalduinen et al., "Structure-Based Annotation of a Novel Sugar Isomerase from the Pathogenic *E. coli* O157:H7," J. Mol. Biol., vol. 401, 2010, pp. 866-881.
"D-lyxose isomerase [*Escherichia coli* FRIK1996]," NCBI, GenBank accession No. EIN16054.1, 2012.
Sujan Chandra Sigdel, "Hybrid Rational Design of Methane Monooxygenase and Isomerase," Department of Chemical Engineering Graduate School of Konkuk University, 2016.

* cited by examiner

*Primary Examiner* — Iqbal H Chowdhury
(74) *Attorney, Agent, or Firm* — Baker & Hostetler LLP

(57) ABSTRACT

The present invention relates to improving the enzymatic activity of *Escherichia coli* O157:H7-derived sugar isomerase by molecular mechanics and site-directed mutagenesis. More particularly, the present invention relates to a sugar isomerase having an enzymatic activity improved by mutation, a nucleic acid molecule encoding the same, a vector comprising the nucleic acid molecule, a transformant comprising the vector, a mutant of the sugar isomerase, and a method for producing L-gulose using the improved sugar isomerase.

1 Claim, 7 Drawing Sheets

Specification includes a Sequence Listing.

MUTANT SUGAR ISOMERASE WITH IMPROVED ACTIVITY, DERIVED FROM *E. COLI*, AND PRODUCTION OF L-GULOSE USING THE SAME

CROSS-REFERENCE TO RELATED APPLICATIONS

This application is National Stage of International patent application PCT/KR2014/005218, filed on Jun. 13, 2014, which claims the benefit of Korean Patent Application No. 10-2014-0071473, filed on Jun. 12, 2014, which are hereby incorporated by reference in their entirety into this application.

SEQUENCE LISTING

The instant application contains a Sequence Listing which has been submitted electronically in ASCII format and is hereby incorporated by reference in its entirety. Said ASCII copy, created on Dec. 12, 2016, is named 087248_003520_SL.txt and is 19,827 bytes in size.

TECHNICAL FIELD

The present invention relates to improving the enzymatic activity of *Escherichia coli* O157:H7-derived sugar isomerase by molecular mechanics and site-directed mutagenesis. More particularly, the present invention relates to a sugar isomerase having an enzymatic activity improved by mutation, a nucleic acid molecule encoding the same, a vector comprising the nucleic acid molecule, a transformant comprising the vector, and a method for producing L-gulose using the improved sugar isomerase and a mutant of the sugar isomerase.

BACKGROUND ART

In recent years, the use of L-carbohydrates and their nucleoside derivatives in the medicine field greatly increased, and modified nucleosides have shown considerable potential as useful antiviral agents. L-gulose is an important key pentose that constitutes a framework in the synthesis of L-ribonucleosides, L-oligoribonucleosides and many other therapeutic agents. L-nucleosides have high stability against attack of in vivo nucleases or the like, compared to D-nucleosides, and thus are highly potential candidates that can be used as therapeutic agents. As L-gulose is known to be highly useful as a raw material for producing medical drugs such as antiviral agents and antibiotics, it has recently attracted a great deal of attention, and thus it is required to establish a highly efficient biological method for producing L-gulose.

L-gulose is present in small amounts in nature, and the stability and conversion efficiency of enzymes capable of producing L-gulose are low. For this reason, it is difficult to commercialize L-gulose. Thus, in enzymatic production methods of producing L-gulose using biocatalysts, it is required to ensure the stability and high activity of enzymes.

PRIOR ART DOCUMENTS

Korean Patent Application No. 10-1997-0018725.

DISCLOSURE

Technical Problem

It is an object of the present invention to improve the enzymatic activity of sugar isomerase, which is involved in bioconversion of L-gulose that is a functional sugar, by site-directed mutagenesis in order to actually use the sugar isomerase as an industrial enzyme.

A second object of the present invention is to provide a recombinant expression vector comprising the improved sugar isomerase gene.

A third object of the present invention is to provide any transgenic strain comprising recombinant *E. coli* transformed with the improved gene.

A forth object of the present invention is to provide recombinant sugar isomerase produced using recombinant *E. coli* transformed with the improved sugar isomerase.

A fifth object of the present invention is to identify residues, which influence the activity of sugar isomerase, by use of the improved sugar isomerase.

Technical Solution

To achieve the above objects, the present invention provides a mutant wherein at least one amino acid selected from among amino acids 56, 92 and 112 of a sugar isomerase of SEQ ID NO: 3 is substituted.

Preferably, threonine at amino acid 56 of SEQ ID NO: 3 is substituted with methionine, methionine at amino acid 92 of SEQ ID NO: 3 is substituted with leucine, and isoleucine at amino acid 112 of SEQ ID NO: 3 is substituted with cysteine, but the scope of the present invention is not limited thereto.

In one embodiment of the present invention, the sugar isomerase is preferably one derived from *Escherichia coli* O157:H7. However, a sugar isomerase produced by a chemical synthetic method or a genetic engineering method also falls within the scope of the present invention.

In another embodiment of the present invention, the mutant sugar isomerase preferably has an amino acid sequence of SEQ ID NO: 5, 7, 9, 11 or 13. However, a mutant having a substitution, deletion, inversion, translocation of one or more amino acids in this amino acid sequence, which provides the effect of the present invention, also falls within the scope of the present invention.

The present invention also provides a gene encoding the sugar isomerase of the present invention.

In one embodiment of the present invention, the gene preferably has a nucleotide sequence of SEQ ID NO: 6, 8, 10, 12 or 14. However, a mutant having a substitution, deletion, inversion, translocation of one or more amino acids in this nucleotide sequence, which provides the effect of the present invention, also falls within the scope of the present invention.

The present invention also provides a recombinant vector comprising the gene of the present invention.

The present invention also provides a method for producing the mutant sugar isomerase of the present invention, and the method comprises a step of transforming the recombinant vector into a microorganism to produce a transformant, and expressing the sugar isomerase of the present invention in the transformant.

The present invention also provides a method of increasing the production of L-gulose from L-sorbose by use of the mutant sugar isomerase of the present invention.

The present invention also provides a composition for producing L-gulose, containing the mutant sugar isomerase of the present invention as an active ingredient.

Hereinafter, the present invention will be described.

The present invention is intended to identify several residues, which play an important role in the activity of sugar isomerase, by use of the sugar isomerase of the present invention, thereby providing a base technology for identification of factors that determine the activity of sugar isomerase.

The present invention provides highly active sugar isomerase by use of the mutant sugar isomerase of the present invention, in which the highly active sugar isomerase may be used to efficiently produce L-gulose.

Hereinafter, the present invention will be described in detail.

Each of SEQ ID NOs: 6, 8, 10, 12 and 14 represents the nucleotide sequences of the mutant sugar isomerase gene of the present invention, and each of SEQ ID NOs: 5, 7, 9, 11 and 13 represents the amino acid sequences of an enzyme which is encoded by the gene. As described above, a polypeptide having the amino acid sequence may have several amino acid mutations, such as deletion, substitution, addition or the like, as long as it has sugar isomerase activity. Furthermore, the scope of the gene of the present invention include, in addition to those having nucleotide sequences encoding the amino acid sequences represented by SEQ ID NOs: 5, 7, 9, 11 and 13, degenerate isomers encoding the same polypeptides having a different degenerate codon. Herein, mutations, such as deletion, substitution, addition or the like, may be introduced by a site-directed mutagenesis method (Current Protocols in Molecular Biology, Vol. 1, pp. 811, 1994) or the like.

The transformed microorganism according to the present invention is obtained by introducing the recombinant vector of the present invention into a host suitable for the expression vector used when constructing the recombinant vector. For example, where bacteria such as *E. coli* are used as a host, the recombinant vector according to the present invention is self-replicable in the host and, at the same time, has components required for expression, for example, a promoter, a DNA containing the sugar isomerase gene, a transcription termination sequence and the like. The expression vector used in the present invention is pET-28a, but any expression vector that satisfies the above-described requirements may be used in the present invention.

Any promoter may be used in the present invention, as long as it may be expressed in a host. Examples of a promoter that may be used in the present invention include promoters derived from *E. coli* or phage, for example, lip promoter, trc promoter, tac promoter, lac promoter, PL promoter, PR promoter, T7 promoter, T3 promoter and the like. To introduce recombinant DNA into bacteria, a calcium chloride technique, an electroporation technique or the like may be used.

The recombinant vector may further contain fragments having various functions for expression inhibition, expression amplification or expression induction, a marker for selection of a transformant, an antibiotic resistance gene, a gene encoding a signal for secretion out of bacterial cells, or the like.

The mutant sugar isomerase according to the present invention is produced in the following manner. Specifically, the production of the mutant sugar isomerase is performed by culturing a transformant obtained by transforming a host with a recombinant vector having a gene encoding the mutant sugar isomerase, producing and accumulating the gene product sugar isomerase in the culture product (cultured cells or culture supernatant), and recovering the sugar isomerase from the culture product.

Culture of the transformant according to the present invention may be performed using a conventional method which is used for culture of a host.

Furthermore, where a microorganism transformed with an expression promoter containing an inducible promoter is cultured, a suitable inducer selected depending on the kind of promoter may be added to a medium. Examples of the inducer include isopropyl-β-D-thiogalactopyranoside (IPTG), kanamycin, and the like.

Recovery and purification of the mutant sugar isomerase may be performed by recovering cells or a supernatant from the obtained culture product, and then performing any one or suitable combination of cell disruption, extraction, affinity chromatography, cation or anion exchange chromatography, gel filtration, and the like.

Confirmation that the obtained purified substance is the desired sugar isomerase may be performed by a conventional method, for example, SDS-polyacrylamide gel electrophoresis, Western blotting, or the like.

In addition, culture of the transformant obtained using a microorganism as a host, production of the sugar isomerase by the transformant, accumulation of the sugar isomerase in the cells, and recovery of the sugar isomerase from the cells, are not limited to the above-described methods.

In the present invention, in order to obtain highly active sugar isomerase and identify several residues that play an important role in the activity of the sugar isomerase, a sugar isomerase gene was cloned from *E. coli* O157:H7. It has been found that a recombinant strain having the above-described gene inserted therein contains several residues playing an important role in the high activity of the enzyme and that a recombinant strain, obtained using a mutant enzyme obtained by mutation of the residues, can exhibit an increased activity of producing L-gulose from L-sorbose.

In the present invention, the use of several sugar isomerase mutants showing high activity could make it possible to increase the activity of the enzymes while increasing the binding affinity for their substrate. This suggests that the mutant sugar isomerase of the present invention overcomes the problems associated with the low enzymatic activity of conventional sugar isomerase, and thus can be advantageously applied for the production of L-gulose from a sugar mixture.

Advantageous Effects

L-gulose which is produced by conventional sugar isomerase is medically and pharmaceutically useful as antiviral agents or the like, but has disadvantages in that it is unstable and has low enzymatic activity.

Accordingly, the present invention is intended to mutate residues playing an important role in the activity of a sugar isomerase derived from *Escherichia coli* O157:H7, thereby developing an improved sugar isomerase having increased enzymatic activity and an increased ability to bind to its substrate. Furthermore, the use of the sugar isomerase mutant and the improved sugar isomerase makes it possible to efficiently produce L-gulose.

BEST MODE

Hereinafter, the present invention will be described in further detail with reference to the following non-limiting examples. It is to be understood, however, that these examples are for illustrative purposes and are not intended to limit the scope of the present invention.

Example 1

Cloning of Sugar Isomerase Gene

*E. coli* O157:H7 was cultured at 37° C. and centrifuged (at 8000×g for 10 minutes) to obtain cells. Genomic DNA was isolated from the obtained cells, and subjected to PCR using primers (EcSI F-5'-GGA TCC ATG AAA CGC TCC GCT A-3' (SEQ ID NO: 1) and EcSI R-5'-GTC GAC GCG GAA CTG GCG GTA T-3' (SEQ ID NO: 2) constructed based on the nucleotide sequence of a gene encoding an *E. coli* O157:H7-derived sugar isomerase. The PCR product, that is, the *E. coli* O157:H7-derived sugar isomerase-encoding gene, was inserted into a pGEM T-easy vector, and the nucleotide sequence thereof was analyzed (SEQ ID NO: 4).

Example 2

Construction of Recombinant Expression Vector and Recombinant Strain

In order to express a large amount of sugar isomerase in *E. coli* by use of the sugar isomerase-encoding gene obtained in Example 1, the sugar isomerase gene was inserted into the BamHI and SalI sites of the expression vector pET-28a (Novagen, Germany) which was then transformed into *E. coli* BL21(DE3) (NEB, Great Britain).

Example 3

Expression and Purification of Recombinant Sugar Isomerase

Figure 1:
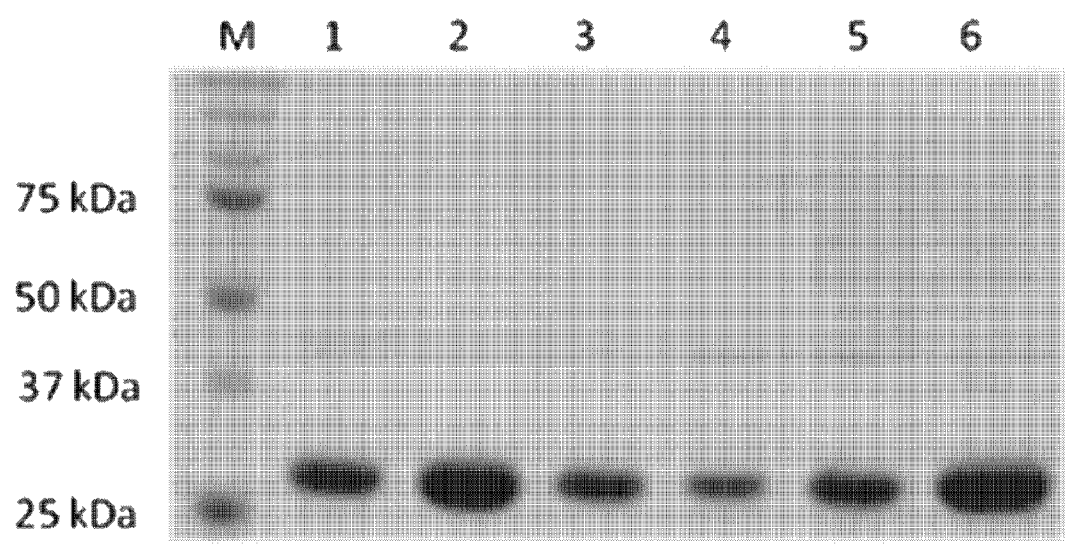
FIG. 1 is an SDS-polyacrylamide gel electrophoresis image of wild-type sugar isomerase and highly active mutants (EcSI, I112C, T56M, M92L, I112C T56M and I112C T56M M92L), derived from *Escherichia coli* O157:H7 strain.

The recombinant strain constructed in Example 2 was inoculated into LB medium and cultured at 37° C. for 24 hours, and then the expressed protein was analyzed on SDS-PAGE gel (FIG. 1).

In order to purify the recombinant sugar isomerase expressed according to the method of Example 3, the cultured recombinant strain solution was centrifuged (at 8000×g for 10 minutes) to collect only cells which were then sonicated to disrupt the *E. coli* cell wall. Next, the cell solution was centrifuged at 20,000×g for 20 minutes to remove the precipitate (cells) and recover the supernatant. Finally, column chromatography using a Ni-NTA Super flow column (GE Healthcare, Great Britain) was performed to purify the recombinant sugar isomerase.

Example 4

Construction of Highly Active Sugar Isomerase Mutant

Example 4-1

Identification of Residues Playing Important Role in Activity

Figure 2:
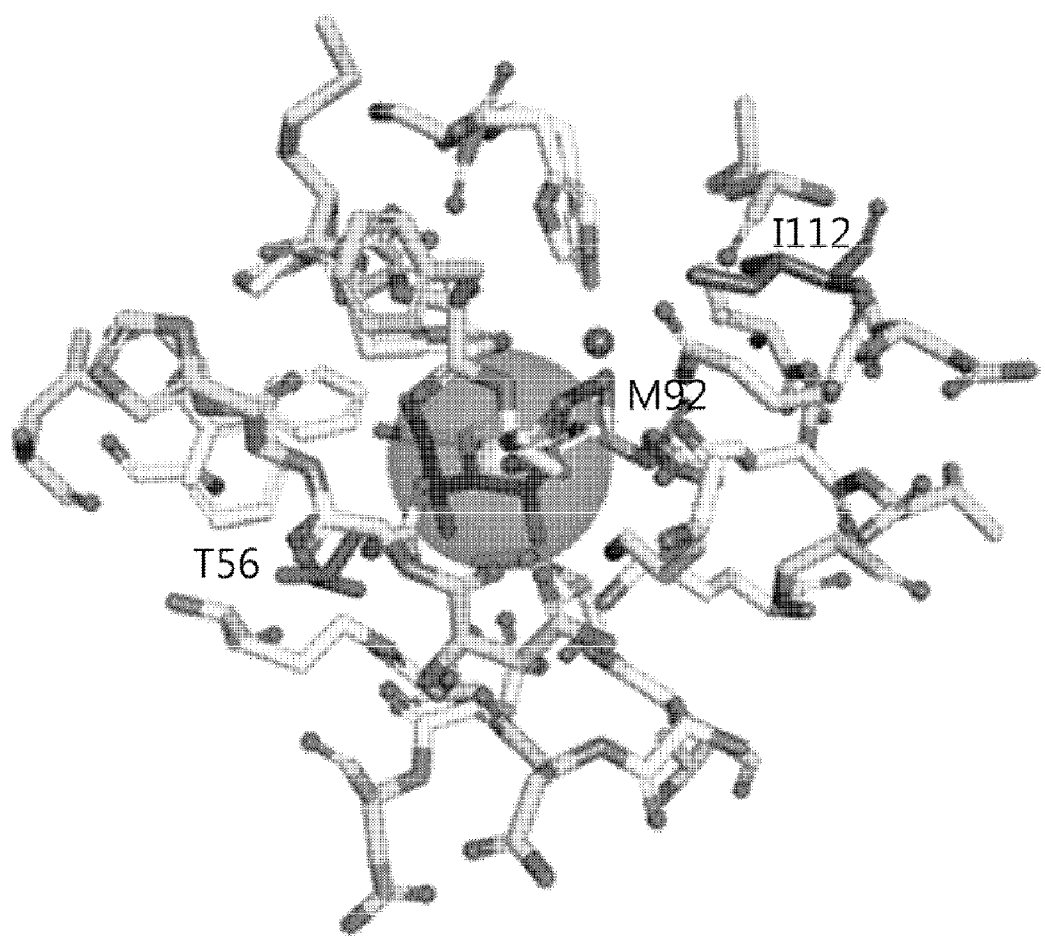
FIGS. 2 and 3 show the results of molecular mechanics-based computer analysis for the active sites of EcSI to which a substrate binds. (A) wild-type strain; and (B) triple mutant EcSI I112C T56M M92L.
Figure 3:
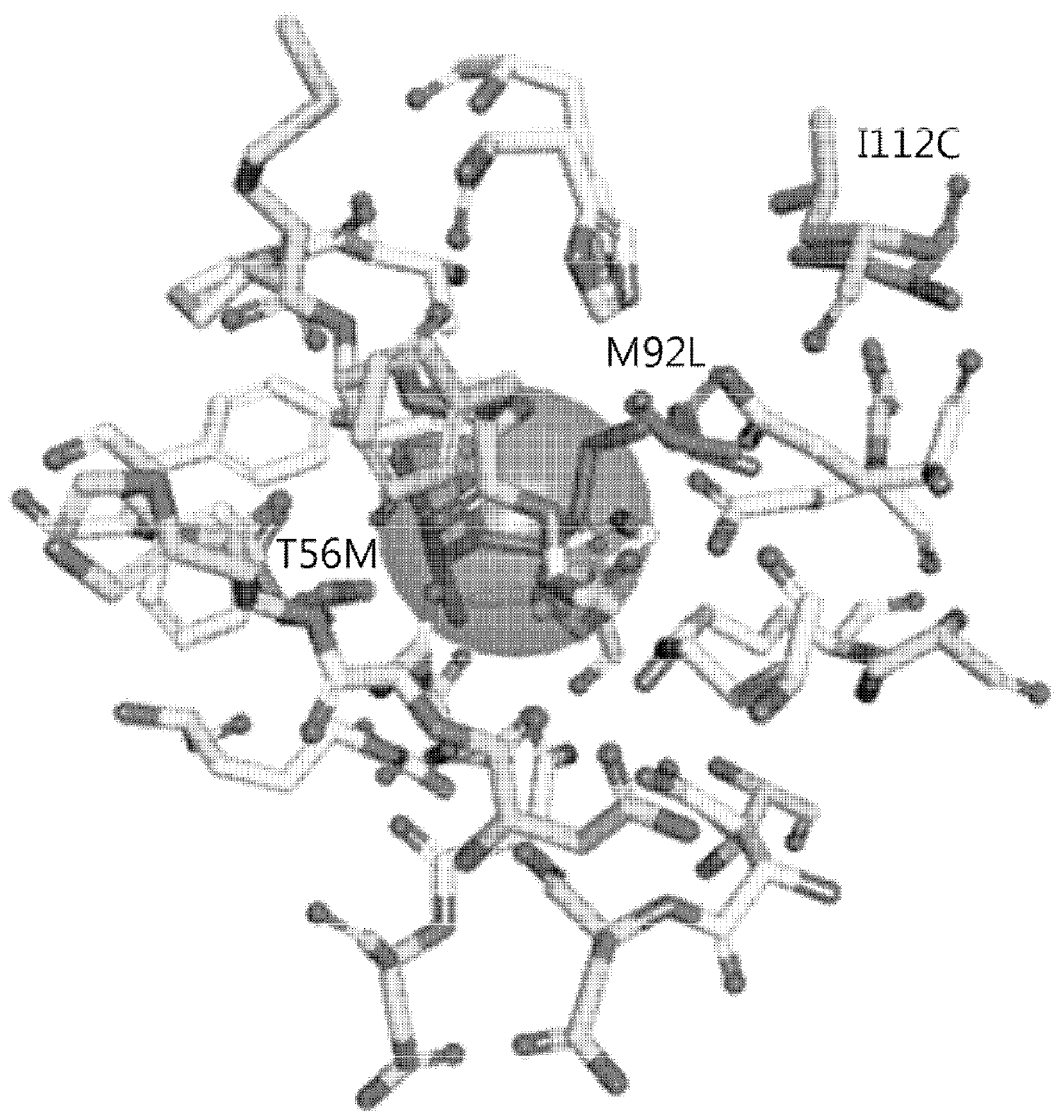
Figure 4:
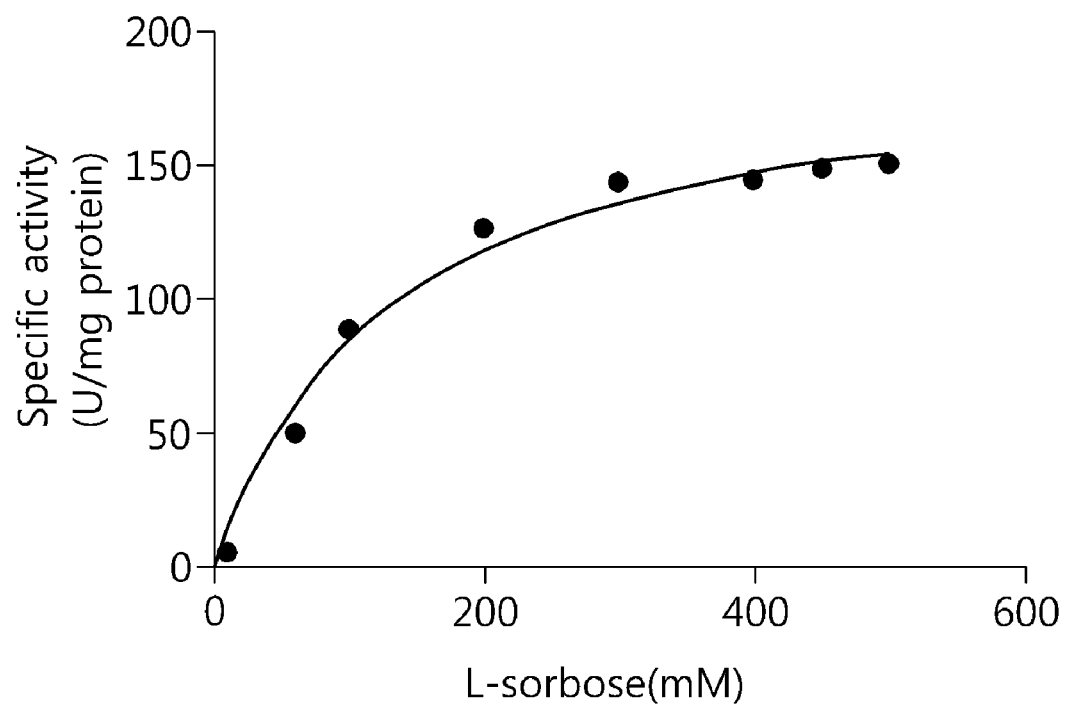
FIG. 4 is a graph showing the kinetic parameters of a wild-type EcSI enzyme.
Figure 5:
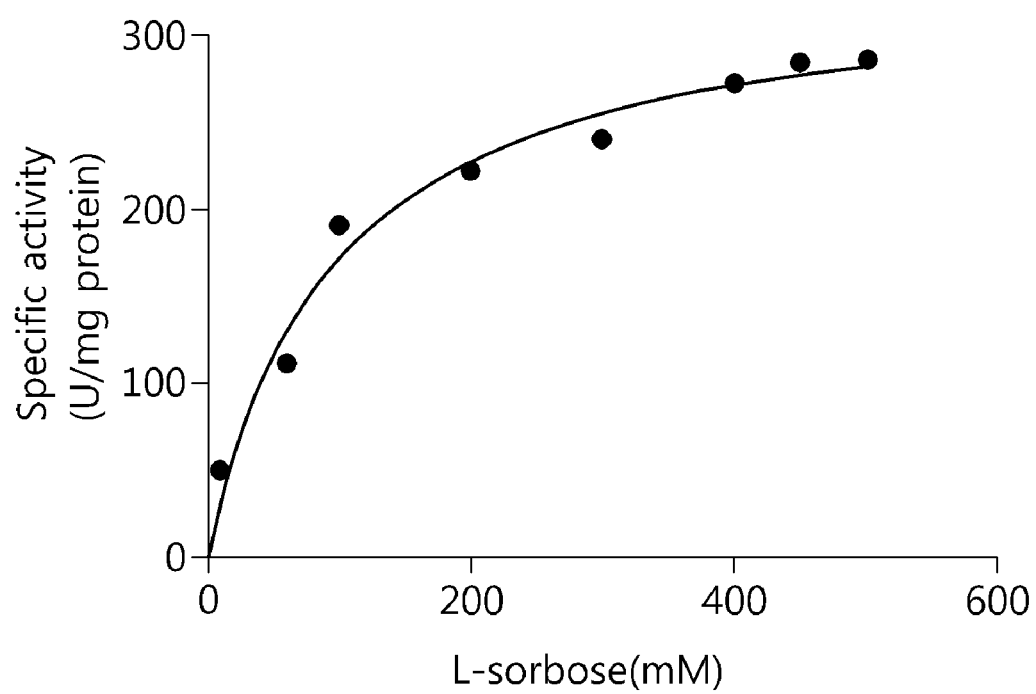
FIG. 5 is a graph showing the kinetic parameters of an EcSI I112C T56M mutant.
Figure 6:
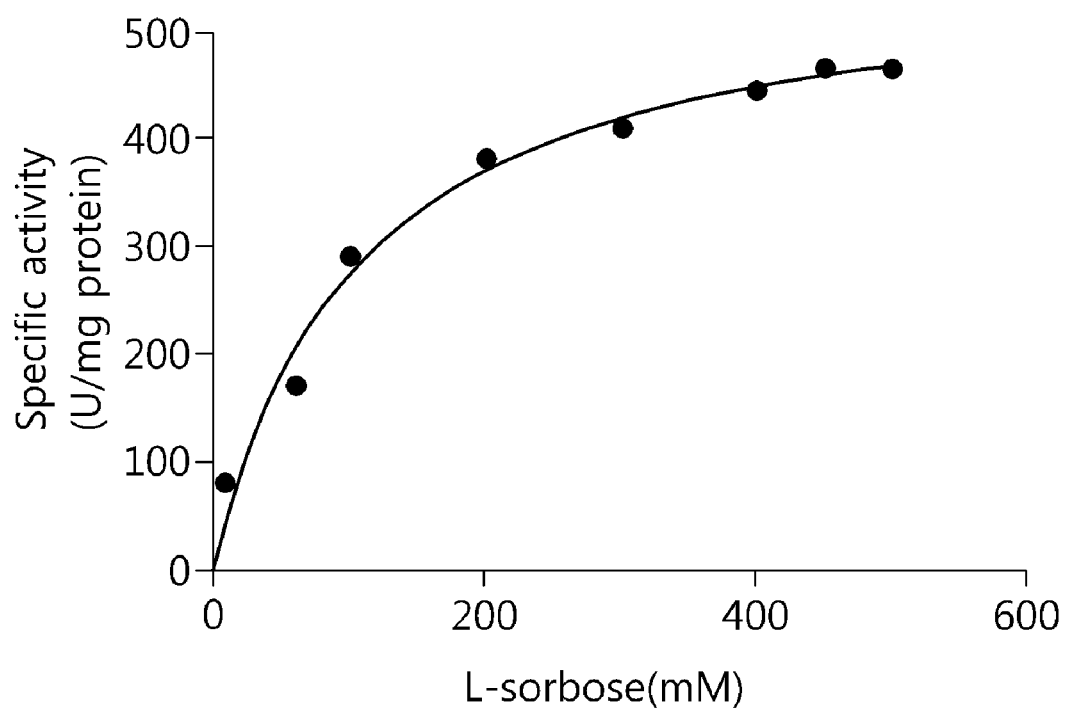
FIG. 6 is a graph showing the kinetic parameters of an EcSI I112C T56M M92L mutant.

In order to identify residues playing an important role in the high activity of the sugar isomerase purified in Example 3, quantum mechanics/molecular mechanics techniques of Discovery Studio 3.1 and Materials Studio 6.0 (Accelrys Inc., San Diego, Calif., USA) were used. As shown in FIGS. 2 and 3, the binding energy (Kcal/mol) of mutants obtained by substituting the residues of the substrate-binding site of the sugar isomerase was compared to the binding energy of a wild-type enzyme. It is known that as the binding energy decreases, the binding affinity increases. As shown in Table 1 below, I112C, T56M and M92L mutant enzymes showed lower binding energy than the wild-type enzyme.

TABLE 1

| Enzyme | Binding energy (Kcal/mol) |
| --- | --- |
| WT | −188 |
| I112C | −194 |
| T56M | −192 |
| M92L | −189 |

Example 4-2

Kinetic Parameters of I112C, T56M and M92L Mutants

Isoleucine at residue 112, which showed the lowest binding energy among the residues of the substrate binding site upon mutation as shown in Example 4-1, was substituted with cysteine, threonine at residue 56 was substituted with methionine, and methionine at residue 92 was substituted with leucine. The mutants were constructed using a site-directed mutagenesis kit (Stratagene, USA). As shown in Table 2 below, it can be seen that the I112C mutant and the T56M mutant had an increased binding affinity for their substrate and increased activity. In addition, residues having the highest kinetic parameter were selected. Using the selected residues, the double mutant I112C T56M and the triple mutant I112C T56M M92L were constructed, and the turnover rates thereof were analyzed. As a result, it could be seen that the turnover rate of the double or triple mutant was higher than that of the single mutant. Table 2 below shows the kinetic parameters of sugar isomerase enzymes.

TABLE 2

| Enzyme | $K_m$ (mM) | $k_{cat}$ (S$^{-1}$) | $k_{cat}/K_m$ (mM$^{-1}$S$^{-1}$) |
| --- | --- | --- | --- |
| EcSI | 133 | 84 | 0.63 |
| I112C | 95 | 88 | 0.92 |
| T56M | 118 | 101 | 0.85 |
| M92L | 149 | 105 | 0.70 |
| I112C T56M | 94 | 144 | 1.53 |
| I112C T56M M92L | 107 | 245 | 2.28 |

Example 5

Production of L-Gulose Using *E. coli* O157:H7-Derived Sugar Isomerase Under Optimal Conditions For the maximum production of L-gulose by use of sugar isomerase, an isomerization reaction was performed under optimal conditions. The reaction was performed in 0.2 M glycin-NaOH buffer (pH 8 buffer), and an experiment for the production of L-gulose was performed by shaking culture at 200 rpm and 40° C. in the presence of 10 mg of sugar isomerase and 74 g/L of the substrate L-sorbose.

Figure 7:
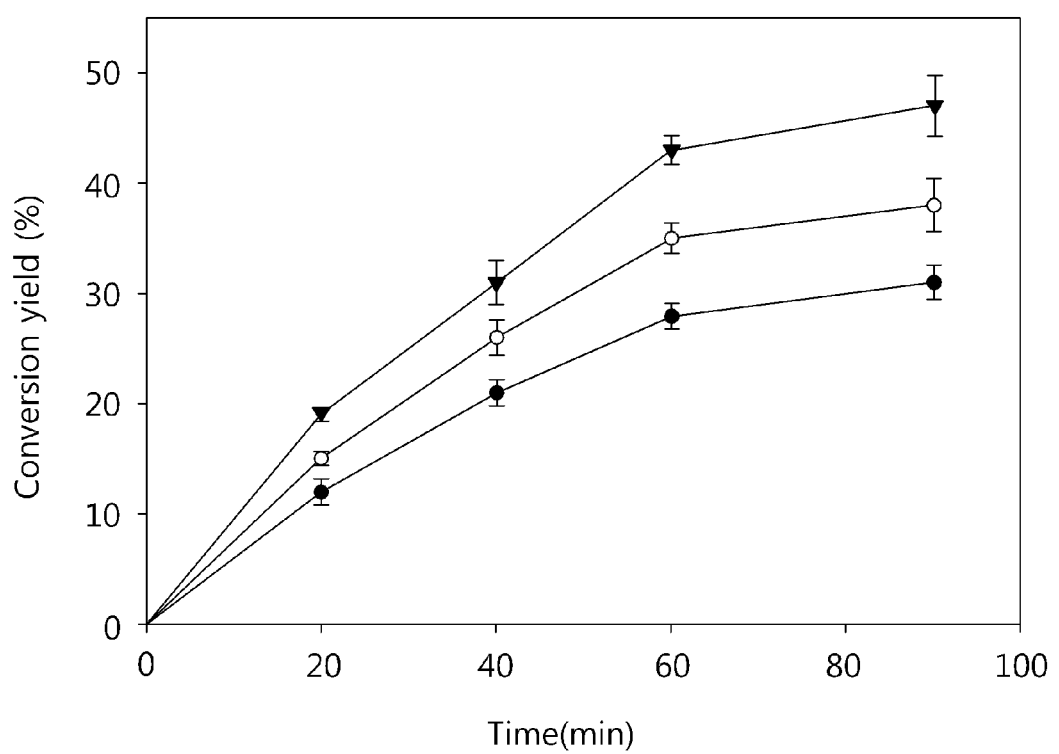
FIG. 7 shows the time-dependent production of L-gulose obtained by the reaction of an *E. coli* O157:H7-derived sugar isomerase under optimal conditions.

As shown in FIG. 7, the time at which the maximum production of L-gulose reached was 90 minutes. EcSI wild-type, the double mutant I112C T56M, and the tripe mutant I112C T56M M92L produced 22 g/L, 28 g/L, and 36 g/L of L-gulose, respectively. Such final yields were much higher than the result reported in a prior document (0.9 g/L) that used mannitol 1-dehydrogenase in the production of L-gulose from L-sorbose.

The invention claimed is:

1. A gene encoding a mutant sugar isomerase consisting of the nucleotide sequence of SEQ ID NO: 6, 8, 10, 12 or 14, wherein the mutant sugar isomerase has isomerase activity.

* * * * *

```
                         SEQUENCE LISTING

<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggatccatga aacgctccgc ta                                                  22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtcgacgcgg aactggcggt at                                                  22

<210> SEQ ID NO 3
<211> LENGTH: 227
<212> TYPE: PRT
<213> ORGANISM: Escherichia coli

<400> SEQUENCE: 3

Met Lys Arg Ser Ala Ile Asn Asp Ile Leu Gly His Thr Arg Gln Phe
1               5                   10                  15

Phe Ser Gln His Asp Val His Leu Pro Pro Phe Ala Ser Phe Ser Pro
                20                  25                  30

Ala Gln Trp Gln Gln Leu Asp Thr Ala Ala Trp Glu Val Phe Asp
            35                  40                  45

Leu Lys Leu Gly Trp Asp Val Thr Ala Phe Gly Arg Asn Asn Phe Ala
    50                  55                  60

Ala His Gly Leu Thr Leu Phe Thr Leu Arg Asn Gly Ser Ala Lys Gly
65                  70                  75                  80

Met Pro Tyr Val Lys Cys Tyr Ala Glu Lys Ile Met His Val Arg Asp
                85                  90                  95

Ala Gln Val Thr Pro Met His Phe His Trp Arg Lys Arg Glu Asp Ile
            100                 105                 110

Ile Asn Arg Gly Gly Gly Asn Leu Ile Val Glu Leu Trp Asn Ala Asp
        115                 120                 125

Ser Asn Glu Gln Thr Ala Asp Ser Asp Ile Thr Val Val Ile Asp Gly
    130                 135                 140

Cys Arg Gln Lys His Thr Ala Gly Ser Gln Leu Arg Leu Ser Pro Gly
145                 150                 155                 160
```

Glu Ser Ile Cys Leu Pro Pro Gly Leu Tyr His Ser Phe Trp Ala Glu
            165                 170                 175

Ala Gly Phe Gly Asp Val Leu Val Gly Val Ser Ser Val Asn Asp
            180                 185                 190

Asp Asp His Asp Asn His Phe Leu Gln Pro Leu Asp Arg Tyr Asn Leu
        195                 200                 205

Ile Asp Glu Asp Glu Pro Ala Gln Leu Val Leu Cys Asn Glu Tyr Arg
210                 215                 220

Gln Phe Arg
225

<210> SEQ ID NO 4
<211> LENGTH: 681
<212> TYPE: DNA
<213> ORGANISM: Escherichia coli

<400> SEQUENCE: 4
atgaaacgct ccgctataaa cgacattctc ggccatacac ggcaattctt ttcgcaacat     60
gacgtacatc tgccgccctt tgccagtttc tcgcctgctc aatggcagca gctcgacacc    120
gccgcgtggg aggaggtttt tgatcttaaa ctcggctggg atgttaccgc ttttggtcgc    180
aacaactttg cagcacacgg gctgacgctg tttaccctac gtaacggctc agcaaaagga    240
atgccgtatg tgaaatgtta cgccgagaag atcatgcatg tgcgcgatgc gcaggtcacg    300
ccaatgcatt tcactggcg taagcgtgag acattatca atcgcggcgg cggtaattta    360
attgttgaac tgtggaatgc cgatagtaac gagcaaacgg ctgatagtga cattacggtg    420
gtgatagacg gctgccgcca gaaacatact gcaggctctc agttgcgcct gtctcccggc    480
gaaagtatct gcctgccgcc cggcctgtat cacagctttt gggcagaagc cggttttggc    540
gatgtgctgg ttggcgaagt ctcttctgtt aatgacgacg accacgataa ccactttta    600 cagccactgg accgctacaa cctgattgac gaagacgaac ctgcacagtt ggtattgtgt    660
aacgaatacc gccagttccg c                                              681

<210> SEQ ID NO 5
<211> LENGTH: 227
<212> TYPE: PRT
<213> ORGANISM: Artificial Sequence
<220> FEATURE:
<223> OTHER INFORMATION: Description of Artificial Sequence: Synthetic
      mutant polypeptide

<400> SEQUENCE: 5

Met Lys Arg Ser Ala Ile Asn Asp Ile Leu Gly His Thr Arg Gln Phe
1               5                   10                  15

Phe Ser Gln His Asp Val His Leu Pro Pro Phe Ala Ser Phe Ser Pro
            20                  25                  30

Ala Gln Trp Gln Gln Leu Asp Thr Ala Ala Trp Glu Glu Val Phe Asp
        35                  40                  45

Leu Lys Leu Gly Trp Asp Val Met Ala Phe Gly Arg Asn Asn Phe Ala
    50                  55                  60

Ala His Gly Leu Thr Leu Phe Thr Leu Arg Asn Gly Ser Ala Lys Gly
65                  70                  75                  80

Met Pro Tyr Val Lys Cys Tyr Ala Glu Lys Ile Met His Val Arg Asp
                85                  90                  95

Ala Gln Val Thr Pro Met His Phe His Trp Arg Lys Arg Glu Asp Ile
            100                 105                 110

-continued

```
Ile Asn Arg Gly Gly Gly Asn Leu Ile Val Glu Leu Trp Asn Ala Asp
            115                 120                 125

Ser Asn Glu Gln Thr Ala Asp Ser Asp Ile Thr Val Val Ile Asp Gly
        130                 135                 140

Cys Arg Gln Lys His Thr Ala Gly Ser Gln Leu Arg Leu Ser Pro Gly
145                 150                 155                 160

Glu Ser Ile Cys Leu Pro Pro Gly Leu Tyr His Ser Phe Trp Ala Glu
                165                 170                 175

Ala Gly Phe Gly Asp Val Leu Val Gly Glu Val Ser Ser Val Asn Asp
            180                 185                 190

Asp Asp His Asp Asn His Phe Leu Gln Pro Leu Asp Arg Tyr Asn Leu
        195                 200                 205

Ile Asp Glu Asp Glu Pro Ala Gln Leu Val Leu Cys Asn Glu Tyr Arg
    210                 215                 220

Gln Phe Arg
225
```

<210> SEQ ID NO 6
<211> LENGTH: 681
<212> TYPE: DNA
<213> ORGANISM: Artificial Sequence
<220> FEATURE:
<223> OTHER INFORMATION: Description of Artificial Sequence: Synthetic
      mutant polynucleotide

<400> SEQUENCE: 6

```
atgaaacgct ccgctataaa cgacattctc ggccatacac ggcaattctt ttcgcaacat      60
gacgtacatc tgccgccctt tgccagtttc tcgcctgctc aatggcagca gctcgacacc     120
gccgcgtggg aggaggtttt tgatcttaaa ctcggctggg atgttatggc ttttggtcgc     180
aacaactttg cagcacacgg gctgacgctg tttaccctac gtaacggctc agcaaaagga     240
atgccgtatg tgaaatgtta cgccgagaag atcatgcatg tgcgcgatgc gcaggtcacg     300
ccaatgcatt tcactggcg taagcgtgag acattatca atcgcggcgg cggtaattta      360
attgttgaac tgtggaatgc cgatagtaac gagcaaacgg ctgatagtga cattacggtg     420
gtgatagacg gctgccgcca gaaacatact gcaggctctc agttgcgcct gtctcccggc     480
gaaagtatct gcctgccgcc cggcctgtat cacagctttt gggcagaagc cggttttggc     540
gatgtgctgg ttggcgaagt ctcttctgtt aatgacgacg accacgataa ccacttttta     600
cagccactgg accgctacaa cctgattgac gaagacgaac ctgcacagtt ggtattgtgt     660
aacgaatacc gccagttccg c                                               681
```

<210> SEQ ID NO 7
<211> LENGTH: 227
<212> TYPE: PRT
<213> ORGANISM: Artificial Sequence
<220> FEATURE:
<223> OTHER INFORMATION: Description of Artificial Sequence: Synthetic
      mutant polypeptide

<400> SEQUENCE: 7

```
Met Lys Arg Ser Ala Ile Asn Asp Ile Leu Gly His Thr Arg Gln Phe
1               5                  10                  15

Phe Ser Gln His Asp Val His Leu Pro Pro Phe Ala Ser Phe Ser Pro
            20                  25                  30

Ala Gln Trp Gln Gln Leu Asp Thr Ala Ala Trp Glu Glu Val Phe Asp
        35                  40                  45
```

Leu Lys Leu Gly Trp Asp Val Thr Ala Phe Gly Arg Asn Asn Phe Ala
 50                  55                  60

Ala His Gly Leu Thr Leu Phe Thr Leu Arg Asn Gly Ser Ala Lys Gly
 65                  70                  75                  80

Met Pro Tyr Val Lys Cys Tyr Ala Glu Lys Ile Leu His Val Arg Asp
                 85                  90                  95

Ala Gln Val Thr Pro Met His Phe His Trp Arg Lys Arg Glu Asp Ile
            100                 105                 110

Ile Asn Arg Gly Gly Gly Asn Leu Ile Val Glu Leu Trp Asn Ala Asp
            115                 120                 125

Ser Asn Glu Gln Thr Ala Asp Ser Asp Ile Thr Val Val Ile Asp Gly
130                 135                 140

Cys Arg Gln Lys His Thr Ala Gly Ser Gln Leu Arg Leu Ser Pro Gly
145                 150                 155                 160

Glu Ser Ile Cys Leu Pro Pro Gly Leu Tyr His Ser Phe Trp Ala Glu
                165                 170                 175

Ala Gly Phe Gly Asp Val Leu Val Gly Glu Val Ser Ser Val Asn Asp
            180                 185                 190

Asp Asp His Asp Asn His Phe Leu Gln Pro Leu Asp Arg Tyr Asn Leu
            195                 200                 205

Ile Asp Glu Asp Glu Pro Ala Gln Leu Val Leu Cys Asn Glu Tyr Arg
210                 215                 220

Gln Phe Arg
225

<210> SEQ ID NO 8
<211> LENGTH: 681
<212> TYPE: DNA
<213> ORGANISM: Artificial Sequence
<220> FEATURE:
<223> OTHER INFORMATION: Description of Artificial Sequence: Synthetic
      mutant polynucleotide

<400> SEQUENCE: 8
atgaaacgct ccgctataaa cgacattctc ggccatacac ggcaattctt ttcgcaacat      60
gacgtacatc tgccgcccct tgccagtttc tcgcctgctc aatggcagca gctcgacacc     120
gccgcgtggg aggaggtttt tgatcttaaa ctcggctggg atgttaccgc ttttggtcgc     180
aacaactttg cagcacacgg gctgacgctg tttaccctac gtaacggctc agcaaaagga     240
atgccgtatg tgaaatgtta cgccgagaag atcctgcatg tgcgcgatgc gcaggtcacg     300
ccaatgcatt ttcactggcg taagcgtgag gacattatca atcgcggcgg cggtaattta     360
attgttgaac tgtggaatgc cgatagtaac gagcaaacgg ctgatagtga cattacggtg     420
gtgatagacg gctgccgcca gaaacatact gcaggctctc agttgcgcct gtctcccggc     480
gaaagtatct gcctgccgcc cggcctgtat cacagctttt gggcagaagc cggttttggc     540
gatgtgctgg ttggcgaagt ctcttctgtt aatgacgacg accacgataa ccactttttta    600 cagccactgg accgctacaa cctgattgac gaagacgaac tgcacagtt ggtattgtgt      660 aacgaatacc gccagttccg c                                               681

<210> SEQ ID NO 9
<211> LENGTH: 227
<212> TYPE: PRT
<213> ORGANISM: Artificial Sequence
<220> FEATURE:
<223> OTHER INFORMATION: Description of Artificial Sequence: Synthetic mutant polypeptide

<400> SEQUENCE: 9

Met Lys Arg Ser Ala Ile Asn Asp Ile Leu Gly His Thr Arg Gln Phe
1               5                   10                  15

Phe Ser Gln His Asp Val His Leu Pro Pro Phe Ala Ser Phe Ser Pro
            20                  25                  30

Ala Gln Trp Gln Gln Leu Asp Thr Ala Ala Trp Glu Glu Val Phe Asp
        35                  40                  45

Leu Lys Leu Gly Trp Asp Val Thr Ala Phe Gly Arg Asn Asn Phe Ala
    50                  55                  60

Ala His Gly Leu Thr Leu Phe Thr Leu Arg Asn Gly Ser Ala Lys Gly
65                  70                  75                  80

Met Pro Tyr Val Lys Cys Tyr Ala Glu Lys Ile Met His Val Arg Asp
                85                  90                  95

Ala Gln Val Thr Pro Met His Phe His Trp Arg Lys Arg Glu Asp Cys
            100                 105                 110

Ile Asn Arg Gly Gly Gly Asn Leu Ile Val Glu Leu Trp Asn Ala Asp
        115                 120                 125

Ser Asn Glu Gln Thr Ala Asp Ser Asp Ile Thr Val Val Ile Asp Gly
    130                 135                 140

Cys Arg Gln Lys His Thr Ala Gly Ser Gln Leu Arg Leu Ser Pro Gly
145                 150                 155                 160

Glu Ser Ile Cys Leu Pro Pro Gly Leu Tyr His Ser Phe Trp Ala Glu
                165                 170                 175

Ala Gly Phe Gly Asp Val Leu Val Gly Glu Val Ser Ser Val Asn Asp
            180                 185                 190

Asp Asp His Asp Asn His Phe Leu Gln Pro Leu Asp Arg Tyr Asn Leu
        195                 200                 205

Ile Asp Glu Asp Glu Pro Ala Gln Leu Val Leu Cys Asn Glu Tyr Arg
    210                 215                 220

Gln Phe Arg
225

<210> SEQ ID NO 10
<211> LENGTH: 681
<212> TYPE: DNA
<213> ORGANISM: Artificial Sequence
<220> FEATURE:
<223> OTHER INFORMATION: Description of Artificial Sequence: Synthetic
      mutant polynucleotide

<400> SEQUENCE: 10
atgaaacgct ccgctataaa cgacattctc ggccatacac ggcaattctt ttcgcaacat     60
gacgtacatc tgccgccctt tgccagtttc tcgcctgctc aatggcagca gctcgacacc    120
gccgcgtggg aggagttttt tgatcttaaa ctcggctggg atgttaccgc ttttggtcgc    180
aacaactttg cagcacacgg gctgacgctg tttaccctac gtaacggctc agcaaaagga    240
atgccgtatg tgaaatgtta cgccgagaag atcatgcatg tgcgcgatgc gcaggtcacg    300
ccaatgcatt tcactggcg taagcgtgag gactgtatca atcgcggcgg cggtaattta    360
attgttgaac tgtggaatgc cgatagtaac gagcaaacgg ctgatagtga cattacggtg    420
gtgatagacg gctgccgcca gaaacatact gcaggctctc agttgcgcct gtctcccggc    480
gaaagtatct gcctgccgcc cggcctgtat cacagctttt gggcagaagc cggttttggc    540
gatgtgctgg ttggcgaagt ctcttctgtt aatgacgacg accacgataa ccactttta    600

```
cagccactgg accgctacaa cctgattgac gaagacgaac ctgcacagtt ggtattgtgt    660
aacgaatacc gccagttccg c                                              681
```

<210> SEQ ID NO 11
<211> LENGTH: 227
<212> TYPE: PRT
<213> ORGANISM: Artificial Sequence
<220> FEATURE:
<223> OTHER INFORMATION: Description of Artificial Sequence: Synthetic
      mutant polypeptide

<400> SEQUENCE: 11

```
Met Lys Arg Ser Ala Ile Asn Asp Ile Leu Gly His Thr Arg Gln Phe
1               5                   10                  15

Phe Ser Gln His Asp Val His Leu Pro Pro Phe Ala Ser Phe Ser Pro
            20                  25                  30

Ala Gln Trp Gln Gln Leu Asp Thr Ala Ala Trp Glu Glu Val Phe Asp
        35                  40                  45

Leu Lys Leu Gly Trp Asp Val Met Ala Phe Gly Arg Asn Asn Phe Ala
    50                  55                  60

Ala His Gly Leu Thr Leu Phe Thr Leu Arg Asn Gly Ser Ala Lys Gly
65                  70                  75                  80

Met Pro Tyr Val Lys Cys Tyr Ala Glu Lys Ile Met His Val Arg Asp
                85                  90                  95

Ala Gln Val Thr Pro Met His Phe His Trp Arg Lys Arg Glu Asp Cys
            100                 105                 110

Ile Asn Arg Gly Gly Gly Asn Leu Ile Val Glu Leu Trp Asn Ala Asp
        115                 120                 125

Ser Asn Glu Gln Thr Ala Asp Ser Asp Ile Thr Val Val Ile Asp Gly
    130                 135                 140

Cys Arg Gln Lys His Thr Ala Gly Ser Gln Leu Arg Leu Ser Pro Gly
145                 150                 155                 160

Glu Ser Ile Cys Leu Pro Pro Gly Leu Tyr His Ser Phe Trp Ala Glu
                165                 170                 175

Ala Gly Phe Gly Asp Val Leu Val Gly Glu Val Ser Ser Val Asn Asp
            180                 185                 190

Asp Asp His Asp Asn His Phe Leu Gln Pro Leu Asp Arg Tyr Asn Leu
        195                 200                 205

Ile Asp Glu Asp Glu Pro Ala Gln Leu Val Leu Cys Asn Glu Tyr Arg
    210                 215                 220

Gln Phe Arg
225
```

<210> SEQ ID NO 12
<211> LENGTH: 681
<212> TYPE: DNA
<213> ORGANISM: Artificial Sequence
<220> FEATURE:
<223> OTHER INFORMATION: Description of Artificial Sequence: Synthetic
      mutant polynucleotide

<400> SEQUENCE: 12

```
atgaaacgct ccgctataaa cgacattctc ggccatacac ggcaattctt ttcgcaacat    60
gacgtacatc tgccgccctt tgccagtttc tcgcctgctc aatggcagca gctcgacacc   120
gccgcgtggg aggaggtttt tgatcttaaa ctcggctggg atgttatggc ttttggtcgc   180
aacaactttg cagcacacgg gctgacgctg tttaccctac gtaacggctc agcaaaagga   240
```

```
atgccgtatg tgaaatgtta cgccgagaag atcatgcatg tgcgcgatgc gcaggtcacg    300
ccaatgcatt ttcactggcg taagcgtgag gactgtatca atcgcggcgg cggtaattta    360
attgttgaac tgtggaatgc cgatagtaac gagcaaacgg ctgatagtga cattacggtg    420
gtgatagacg gctgccgcca gaaacatact gcaggctctc agttgcgcct gtctcccggc    480
gaaagtatct gcctgccgcc cggcctgtat cacagctttt gggcagaagc cggttttggc    540
gatgtgctgg ttggcgaagt ctcttctgtt aatgacgacg accacgataa ccacttttta    600
cagccactgg accgctacaa cctgattgac gaagacgaac ctgcacagtt ggtattgtgt    660
aacgaatacc gccagttccg c                                              681
```

<210> SEQ ID NO 13
<211> LENGTH: 227
<212> TYPE: PRT
<213> ORGANISM: Artificial Sequence
<220> FEATURE:
<223> OTHER INFORMATION: Description of Artificial Sequence: Synthetic
      mutant polypeptide

<400> SEQUENCE: 13

Met Lys Arg Ser Ala Ile Asn Asp Ile Leu Gly His Thr Arg Gln Phe
1               5                   10                  15

Phe Ser Gln His Asp Val His Leu Pro Pro Phe Ala Ser Phe Ser Pro
                20                  25                  30

Ala Gln Trp Gln Gln Leu Asp Thr Ala Ala Trp Glu Glu Val Phe Asp
            35                  40                  45

Leu Lys Leu Gly Trp Asp Val Met Ala Phe Gly Arg Asn Asn Phe Ala
    50                  55                  60

Ala His Gly Leu Thr Leu Phe Thr Leu Arg Asn Gly Ser Ala Lys Gly
65                  70                  75                  80

Met Pro Tyr Val Lys Cys Tyr Ala Glu Lys Ile Leu His Val Arg Asp
                85                  90                  95

Ala Gln Val Thr Pro Met His Phe His Trp Arg Lys Arg Glu Asp Cys
            100                 105                 110

Ile Asn Arg Gly Gly Gly Asn Leu Ile Val Glu Leu Trp Asn Ala Asp
        115                 120                 125

Ser Asn Glu Gln Thr Ala Asp Ser Asp Ile Thr Val Val Ile Asp Gly
    130                 135                 140

Cys Arg Gln Lys His Thr Ala Gly Ser Gln Leu Arg Leu Ser Pro Gly
145                 150                 155                 160

Glu Ser Ile Cys Leu Pro Pro Gly Leu Tyr His Ser Phe Trp Ala Glu
                165                 170                 175

Ala Gly Phe Gly Asp Val Leu Val Gly Glu Val Ser Ser Val Asn Asp
            180                 185                 190

Asp Asp His Asp Asn His Phe Leu Gln Pro Leu Asp Arg Tyr Asn Leu
        195                 200                 205

Ile Asp Glu Asp Glu Pro Ala Gln Leu Val Leu Cys Asn Glu Tyr Arg
    210                 215                 220

Gln Phe Arg
225

<210> SEQ ID NO 14
<211> LENGTH: 681
<212> TYPE: DNA
<213> ORGANISM: Artificial Sequence
<220> FEATURE:

<223> OTHER INFORMATION: Description of Artificial Sequence: Synthetic mutant polynucleotide

<400> SEQUENCE: 14

```
atgaaacgct ccgctataaa cgacattctc ggccatacac ggcaattctt ttcgcaacat      60
gacgtacatc tgccgcsctt tgccagtttc tcgcctgctc aatggcagca gctcgacacc     120
gccgcgtggg aggaggtttt tgatcttaaa ctcggctggg atgttatggc ttttggtcgc     180
aacaactttg cagcacacgg gctgacgctg tttaccctac gtaacggctc agcaaaagga     240
atgccgtatg tgaaatgtta cgccgagaag atcctgcatg tgcgcgatgc gcaggtcacg     300
ccaatgcatt ttcactggcg taagcgtgag gactgtatca atcgcggcgg cggtaattta     360
attgttgaac tgtggaatgc cgatagtaac gagcaaacgg ctgatagtga cattacggtg     420
gtgatagacg gctgccgcca gaaacatact gcaggctctc agttgcgcct gtctcccggc     480
gaaagtatct gcctgccgcc cggcctgtat cacagctttt gggcagaagc cggttttggc     540
gatgtgctgg ttggcgaagt ctcttctgtt aatgacgacg accacgataa ccacttttta     600
cagccactgg accgctacaa cctgattgac gaagacgaac ctgcacagtt ggtattgtgt     660
aacgaatacc gccagttccg c                                               681
```